United States Patent [19]

Hoppe et al.

[11] Patent Number: 4,844,711

[45] Date of Patent: Jul. 4, 1989

[54] HAIR COLORANTS AND METHODS OF COLORING HAIR

[75] Inventors: Udo Hoppe, Hamburg; Klaus Körbächer, Hamburg-Schenefeld; Karl-Heinz Schrader, Holzminden, all of Fed. Rep. of Germany

[73] Assignee: Beiersdorf AG, Hamburg, Fed. Rep. of Germany

[21] Appl. No.: 142,973

[22] Filed: Jan. 12, 1988

[30] Foreign Application Priority Data

Jan. 16, 1987 [DE] Fed. Rep. of Germany ....... 3701098

[51] Int. Cl.$^4$ ................................................ A61K 7/13
[52] U.S. Cl. .......................................... 8/406; 8/407; 8/408
[58] Field of Search ............................ 8/406, 407, 408

[56] References Cited

U.S. PATENT DOCUMENTS 2,817,342 12/1957 Henkin .
3,839,220 10/1974 Barchas .
3,957,424 5/1976 Zeffren et al. .......................... 8/416
4,129,415 12/1978 Westman .............................. 8/127.6
4,331,167 5/1982 Wajaroff .............................. 424/70
4,466,806 8/1984 Bugaut et al. .......................... 8/406

FOREIGN PATENT DOCUMENTS 1229980 8/1960 Fed. Rep. of Germany .
124794 3/1964 Fed. Rep. of Germany .
140726 1/1974 Netherlands .
1295038 11/1972 United Kingdom .

OTHER PUBLICATIONS

Hackh's Chemical Dictionary 4th Edition, 1969, "Enzyme", p. 242.

*Primary Examiner*—Paul Lieberman
*Assistant Examiner*—Christine A. Skane
*Attorney, Agent, or Firm*—Sprung Horn Kramer & Woods

[57] ABSTRACT

A hair colorant based oxidative dyes, in which colorant the alkaline pH necessary for coloring is not produced until during application by enzymatic methods, and a method of coloring hair.

8 Claims, No Drawings

HAIR COLORANTS AND METHODS OF COLORING HAIR

The invention relates to a hair colorant based on oxidative dyes in which the alkaline pH necessary for colouring is first produced during use by enzymatic methods through the action of urease on urea, and a method of colouring hair using such a hair colorant.

To a large extent, colouring of hair is carried out using so-called oxidative dyes since the latter provide a colouring result having intensive colours of high colour fastness. In this method, the oxidative dyes are produced during the colouring process through oxidative coupling of a developer component and a coupler component. Such coupler and developer components for achieving a very wide variety of colour shades, collectively called hair dye intermediates below, are described in large number in the literature.

Although oxidative coupling, i.e. development of the colouring, can in principle also take place by means of atmospheric oxygen, chemical oxidants are employed in most cases. In particular, oxidants based on hydrogen peroxide have proven successful here, preferably addition compounds of hydrogen peroxide with urea, melamine or sodium borate in addition to hydrogen peroxide itself.

For practical application as hair colorants, the dye intermediates are incorporated into a suitable cosmetic base, which can be a solution, a cream or a gel depending on the type of the final product desired. The oxidant is then added to this preparation immediately before application to the hair.

Such hair colorants from the prior art are normally adjusted to an alkaline pH, preferably through addition of ammonia or organic amines, such as, for example, monoethanolamine.

Although this alkaline pH of conventional hair-care agents leads to a smooth course of the colour-forming oxidation reaction and also to good take-up of the hair dye as a consequence of swelling of the hair in the alkaline medium, it also has not inconsiderable disadvantages: due to the considerable deviation from the skin-physiological, slightly acidic pH, the head skin and the hair are subjected to very hostile conditions. For the same reason, application of such a hair colorant using unprotected hands is not possible without further measures, which makes self-application to the hair and application other than in a hairdressing salon more difficult.

The present invention therefore had the object of providing a hair colorant based on oxidative dyes which, compared with the prior art, causes lower alkali exposure of the hair and is thus also milder and is better tolerated by the skin, and at the same time the colouring result is of at least equal or better quality.

Surprisingly, it has now been found that such a hair colorant can be provided by selecting a composition in which, starting from a basic composition buffered in the acidic region, the alkaline pH is first produced during the colouring process by enzymatic methods through the action of urease on urea.

The invention therefore relates to a hair colorant based on oxidative dyes, characterized by
(a) a basic composition which is buffered in the acidic region by means of a suitable buffer mixture and which, in addition, contains the hair dye intermediates and urea,
(b) urease, and
(c) an oxidant which releases hydrogen peroxide and which is microencapsulated in an acid-stable material which is soluble in alkaline media, the three components (a), (b) and (c) first being mixed immediately prior to the colouring process.

The basic composition of the hair colorant according to the invention is a gel, a cream or a surfactant-containing, foaming solution, such as, for example, a shampoo, depending on the type of the final product desired. This basic material contains, in amounts which are conventional for this purpose, the components which are known from the prior art and which are suitable for application to hair. Components of such basic compositions are, for example:

wetting agents and emulsifiers, such as ionic and nonionic surfactants, for example alkylsulphonates, fatty alcohol sulphates, fatty alcohol polyglycol ether sulphates, ethoxylation products of fatty alcohols, fatty acids or alkylphenols, sorbitan fatty acid esters, fatty acid partial glycerides and fatty acid alkanolamides.

Thickeners, for example cellulose derivatives, starch, fatty alcohols, paraffin oils and fatty acids.

Reducing agents, for example sodium sulphite

Perfume oils

Hair-care additives, for example water-soluble cationic polymers, protein derivatives, lecithin, cholesterol and pantothenic acid Solvents, for example water or lower alcohols.

According to the invention, the basic composition is adjusted to an acidic pH, preferably in the pH range 4.9–6.9, in particular in the pH range 6.0–6.8, by means of a buffer mixture. The proportion of buffer mixture in the basic composition is preferably 2–25% by weight. Preferably suitable buffer mixtures are citrate or phosphate buffers, it being possible for the components of the buffer mixture either to be admixed as pure substances with the remaining components of the basic composition or to be added as an aqueous solution.

In particular, the buffer mixture employed is an aqueous solution which contains 0.7–1.0% by weight of citric acid and 3.4–4.3% by weight of diammonium hydrogen phosphate, in a particularly preferred embodiment having a citric acid:diammonium hydrogen phosphate ratio of 1:4.4–1:4.9.

In addition, the basic composition of the hair colorant according to the invention contains urea in an amount of preferably 2–20% by weight, in particular 2 to 6% by weight.

Furthermore, the basic composition contains the hair dye intermediates, more specifically, according to the invention, preferably containing 0.01 to 5.0% by weight, in particular 0.05 to 3.0% by weight, of one or more conventional developer components and preferably 0.01 to 3.0% by weight, in particular 0.05 to 2.0% by weight, of one or more conventional coupler components. The developer component(s) : coupler component(s) molar ratio in the hair colorant according to the invention is generally about 1:1, but an excess of one or other hair dye intermediates is not disadvantageous.

In the context of the invention, all conventional developer and coupler components which are known to those skilled in the art can in principle be employed, but, depending on the colour desired to be conferred, the developer component(s) are selected from the group comprising the p-toluylenediamines, the p-phenylenediamines, the 2,5-diaminopyridines or the p-aminophenols as the free base or in the form of a cosmetically acceptable salt, and the coupler component(s) are selected from the group comprising the resorcinols, the m-aminophenols, the m-phenylenediamines, the 2,3-diamino-6-methoxypyridines or alpha-naphthol.

In order to produce specific colour shades, it may in addition be expedient to add to the basic composition according to the invention small amounts of one or more direct-action hair dyes in addition to the hair dye intermediates mentioned above.

The second component of the hair colorant according to the invention is the enzyme urease, in an amount of preferably 0.01 to 0.20 parts by weight, in particular 0.05 to 0.15 parts by weight, per 100 parts by weight of the basic composition. In a specific embodiment of the invention, which is particularly suitable for colouring when "greasy" hair shafts are present, component (b) is the enzyme urease, preferably in the abovementioned amounts, mixed with the enzyme lipase, the lipase being employed in an amount from preferably 0.01 to 0.1 part by weight, in particular 0.03 to 0.08 part by weight, per 100 parts by weight of the basic composition, and the two enzymes preferably being mixed in the dry form. In a further specific embodiment of the invention, the enzyme or the enzyme mixture can be employed diluted with an inert solid, for example finely divided silicon dioxide.

The third component of the hair colorant according to the invention comprises a microencapsulated oxidant which releases hydrogen peroxide, preferably an addition product of hydrogen peroxide on urea, melamine or sodium borate, in particular sodium percarbonate or carbamide peroxide. It is essential for the present invention that a material is used for the microencapsulation which is stable in an acidic environment and that the encapsulated oxidant is only liberated at an alkaline pH, since the urease would otherwise be prematurely deactivated. In a preferred fashion according to the invention, alkali-soluble acrylic resins are therefore employed for the microencapsulation of the oxidant. Such materials are commercially available, for example, under the name Eudragit$^R$ S (Messrs. Röhm, Darmstadt). The hair colorant according to the invention preferably contains 5-15 parts by weight, in particular 8-11 parts by weight, of the microencapsulated, hydrogen peroxide-releasing oxidant per 100 parts by weight of the basic composition.

The three components are prepared separately and until use stored in separate packages, or preferably in a suitable 3-component pack, so that they cannot come into direct contact with one another.

The basic composition is prepared by initially mixing all components with the exception of the hair dye intermediates, to give a homogeneous mixture, preferably with gentle warming, in particular at temperatures from 30°–50° C. In specific cases, it may be expedient to first prepare a mixture of urea and buffer mixture, which is then combined with the remaining components. The hair dye intermediates are preferably then incorporated into the mixture thus obtained.

The urease or the urease/lipase mixture prepared by dry mixing is present in the form of a finely divided powder, which is mixed, if appropriate, with the solid used as diluent.

The hydrogen peroxide-releasing oxidant is microencapsulated by a conventional process, preferably using the fluidized bed process.

Hair-colouring using the hair colorant according to the invention is carried out by mixing the 3 components immediately before use and subsequently applying and distributing the mixture on the hair. As is known to those skilled in the art, the necessary amount of hair colorant depends on the length of hair to be coloured. The application temperatures are preferably in a range from 15°–40° C. After allowing a time of preferably 15–45 minutes, in particular 20–35 minutes, for the hair colorant to act, it is removed by rinsing, and the hair is then washed, if appropriate, using a mild shampoo, rinsed again, and dried.

The hair colorant according to the invention is milder and better tolerated compared to hair colorants known hitherto, without the colouring result having to suffer. On the contrary, improved colouring is apparent in the region of the growing hair roots when the colorant according to the invention is used. A further advantage is the reduced problem of odours caused by the ammonia odour occurring during application.

The following examples are intended to illustrate the invention without representing a limitation (PW denotes parts by weight).

EXAMPLE 1

Colouring gel:

The basic composition is prepared by mixing the belowmentioned components while warming gently (40°):

| Raw material | % by weight |
|---|---|
| Sodium sulphite | 0.60 |
| Isopropyl alcohol | 10.00 |
| Coconut fatty acid polydiethanolamide | 35.00 |
| Perfume oil composition | 1.30 |
| Buffer solution | 20.00 |
| Urea | 5.00 |
| Cetyltrimethylammonium chloride (30% strength) | 10.00 |
| p-Phenylenediamine dihydrochloride | 0.07 |
| alpha-Naphthol | 0.04 |
| Chlororesorcinol | 0.04 |
| Water | to 100.00 |

During this preparation, the hair dye intermediates p-phenylenediamine dihydrochloride, alpha-naphthol and chlororesorcinol are the last to be incorporated into the solution of the remaining components.

The buffer solution used is an aqueous solution containing 0.95% by weight of citric acid and 4.30% by weight of diammonium hydrogen phosphate.

The basic composition has a pH of 6.5.

Immediately before use, 0.07 PW of urease and 8.6 PW of microencapsulated carbamide peroxide are added per 100 PW of the basic composition, and the components are mixed and applied to the hair. For one hair colouring operation, about 50 g of basic composition and the corresponding amounts of urease and carbamide peroxide are required. The result is a light-blond colour on white hair.

Due to the reaction of urease and urea, the pH increases from 6.5 initially (basic composition) to 8.9 to 9.1.

EXAMPLE 2

Colouring shampoo, light blond:

The basic composition has the following composition:

| Raw material | % by weight |
| --- | --- |
| Sodium sulphite | 0.44 |
| Isopropyl alcohol | 7.34 |
| Perfume oil composition | 0.73 |
| EDTA | 0.15 |
| Condensation product of C12–C18-fatty alcohol with 3 moles of ethylene oxide | 55.04 |
| Urea | 5.62 |
| Buffer solution (analogous to Example 1) | 22.48 |
| p-Phenylenediamine dihydrochloride | 0.22 |
| Resorcinol | 0.009 |
| p-Nitro-o-aminophenol | 0.11 |
| o-Nitro-p-phenylenediamine | 0.01 |
| Water | to 100.00 |

The composition is prepared by initially mixing the 5 first-mentioned components. The buffer solution, mixed with the urea, and then the hair dye intermediates are subsequently added, and all components are mixed homogeneously.

Immediately before use, 0.1 PW of urease, 0.05 PW of lipase and 9.0 PW of microencapsulated carbamide peroxide are added per 100 PW of basic composition, and the components are mixed and applied to the hair.

EXAMPLE 3

Hair dye:

The basic composition has the following composition:

| Raw material | % by weight |
| --- | --- |
| Sodium sulphite | 0.50 |
| Cetyl/stearyl alcohol | 10.50 |
| Sodium cetylstearylsulphate | 1.50 |
| Paraffin oil perliquidum | 7.50 |
| Wool wax alcohol | 3.75 |
| EDTA | 0.22 |
| Perfume oil composition | 0.45 |
| Urea | 5.00 |
| Buffer solution (analogous to Example 1) | 20.00 |
| p-Toluylenediamine sulphate | 1.00 |
| m-Phenylenediamine | 0.50 |
| Water | to 100.00 |

The composition is prepared by initially mixing the 7 first-mentioned components with the water. The buffer solution, mixed with the urea, and then the hair dye intermediates are subsequently added, and all components are mixed homogeneously. The basic composition has a pH of 6.3.

Application takes place as described in Example 1, 0.1 PW of urease, 0.05 PW of lipase and 9.0 PW of carbamide peroxide being added per 100 PW of the basic composition. The result is a blue colouring on white human hair.

EXAMPLE 4

Colouring shampoo gel:

The basic composition has the following composition:

| Raw material | % by weight |
| --- | --- |
| Condensation product of nonylphenol with 4 moles of ethylene oxide | 27.00 |
| Condensation product of nonylphenol with 9 moles of ethylene oxide | 23.00 |
| Isopropyl alcohol | 16.44 |
| Ammonium hydroxide, 25% strength | 11.00 |
| p-Toluylenediamine | 1.40 |
| m-Phenylenediamine | 0.05 |
| Resorcinol | 0.06 |
| m-Aminophenol | 0.22 |
| p-Aminophenol | 0.23 |
| Ethylenediaminetetraacetic acid | 0.2 |
| Urea | 2.0 |
| Sodium sulphite | 1.0 |
| Water | 15.3 |
| Citric acid | 0.38 |
| Diammonium hydrogen phosphate | 1.72 |

In order to prepare the basic composition, all raw materials are homogeneously mixed consecutively at about 40° C.

This basic composition is mixed immediately before use with 9 PW of microencapsulated carbamide peroxide, 0.1 PW of urease and 0.05 PW of lipase, and the mixture is applied to the hair. A brown-red gel, which is active for colouring for about 30 minutes, is obtained while the pH increases slowly. 90% white hair is coloured chestnut brown.

We claim:

1. Hair colorant based on oxidative dyes, characterized by
   (a) a basic composition which is buffered in the acidic region by means of a suitable buffer mixture and which, in addition, contains the hair dye intermediates and 2–20% by weight of urea,
   (b) 0.01 to 0.20 parts by weight of urease per 100 parts by weight of the basic composition, and
   (c) 5 to 15 parts by weight, per 100 parts by weight of the basic composition, of an oxidant which releases hydrogen peroxide and which is microencapsulated in an acid-stable material, the microcapsules being soluble in alkaline media, and releasing hydrogen peroxide subsequent to an increase in pH resulting from the reaction of urea and urease,
   the three components (a), (b) and (c) first being mixed immediately prior to the colouring process.

2. Hair colorant according to claim 1, characterized in that the basic composition is buffered at a pH of 4.9–6.9.

3. Hair colorant according to claim 1, characterized in that it contains, as components (b), a mixture of urease and lipase, the lipase being employed in an amount from 0.01 to 0.1 part by weight, relative to 100 parts by weight of the basic composition.

4. Hair colorant according to claim 1, characterized in that the hydrogen peroxide-releasing oxidant is sodium percarbonate or carbamide peroxide.

5. Hair colorant according to claim 1, characterized in that the buffer mixture employed is an aqueous solution of 0.7 to 1.0% by weight of citric acid and 3.4 to 4.3% by weight of diammonium hydrogen phosphate in an amount of 2 to 25% by weight of the basic composition.

6. Process for colouring hair using oxidative dyes, characterized in that a colorant according to claim 1 is applied to the hair and rinsed out after allowing 15–45 minutes for the colorant to act, and the hair is washed, if appropriate, rinsed again and subsequently dried.

7. Hair colorant according to claim 1, characterized in that it contains 0.005 to 0.15 part by weight of urease per 100 parts by weight of the basic composition.

8. Hair colorant according to claim 1, characterized in that it contains 8–11 parts by weight of the microencapsulated, hydrogen peroxide-releasing oxidant per 100 parts by weight of the basic composition.

* * * * *